(12) United States Patent
Wheatley et al.

(10) Patent No.: US 9,295,385 B2
(45) Date of Patent: Mar. 29, 2016

(54) IMAGING PROBES AND ASSOCIATED DEVICES, SYSTEMS, AND METHODS UTILIZING SPEAKER ACTUATORS

(71) Applicant: NOVARTIS AG, Basel (CH)

(72) Inventors: Barry Lynn Wheatley, Oceanside, CA (US); Vinh Vu, Garden Grove, CA (US)

(73) Assignee: Novartis AG (CH)

( * ) Notice: Subject to any disclaimer, the term of this patent is extended or adjusted under 35 U.S.C. 154(b) by 141 days.

(21) Appl. No.: 14/280,307

(22) Filed: May 16, 2014

(65) Prior Publication Data

US 2015/0327760 A1    Nov. 19, 2015

(51) Int. Cl.
  *A61B 5/00*    (2006.01)
  *A61B 3/10*    (2006.01)
  *A61B 3/00*    (2006.01)

(52) U.S. Cl.
  CPC .............. *A61B 3/102* (2013.01); *A61B 3/0008* (2013.01)

(58) Field of Classification Search
  CPC ............... A61B 19/5244; A61B 18/20; A61B 2018/2211; A61B 2018/0293; A61B 5/6848; A61B 17/06109; A61B 2018/1425; A61B 2019/5206

USPC .................................................. 600/478, 476
See application file for complete search history.

(56) References Cited

U.S. PATENT DOCUMENTS 6,564,087 B1    5/2003  Pitris et al.
8,655,431 B2 *  2/2014  Joos ...................... A61B 18/20
                                                      600/108

* cited by examiner

*Primary Examiner* — Hung Dang

(57) ABSTRACT

Devices, systems, and methods that utilize a speaker to impart motion to an optical fiber positioned within an imaging probe are provided. In some embodiments, an ophthalmic imaging apparatus comprises an optical probe having a handle sized and shaped for handheld grasping by a user; and a cannula coupled to the handle, the cannula sized and shaped for insertion into an eye to be treated; an optical fiber positioned at least partially within the optical probe, the optical fiber configured to receive an imaging light from an imaging light source and guide the imaging light to an optical element positioned within the cannula of the optical probe; and an actuator system configured to impart motion to the optical fiber, the actuator system including a speaker positioned within the optical probe.

21 Claims, 3 Drawing Sheets

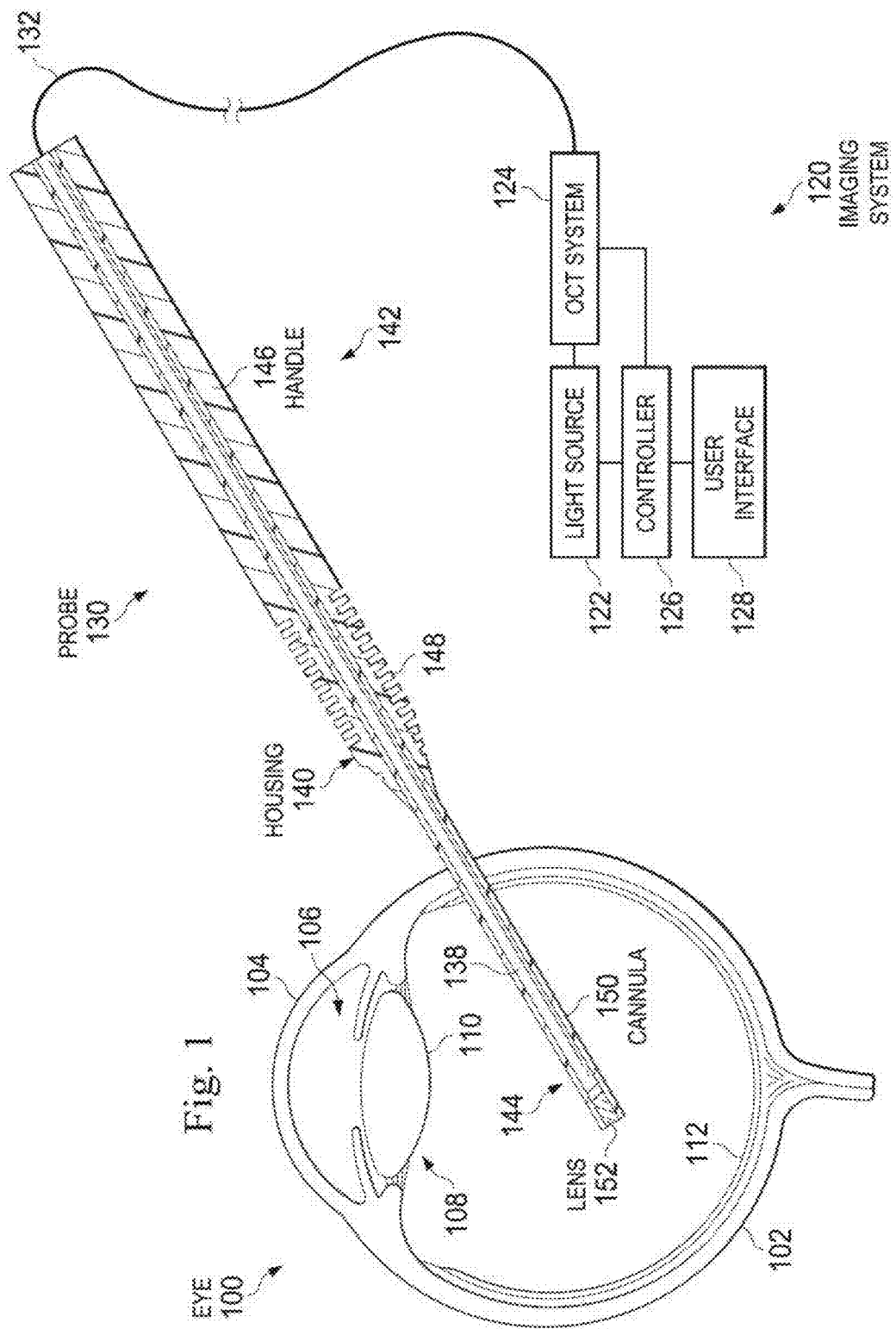

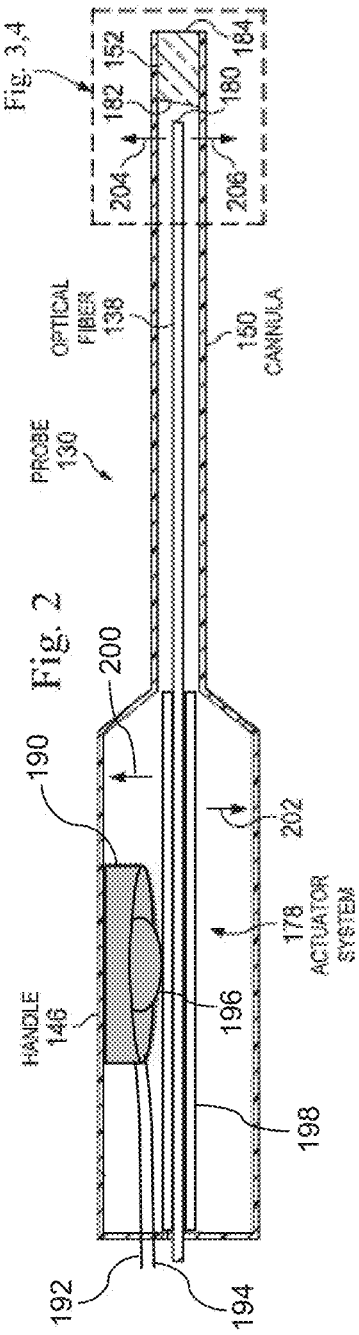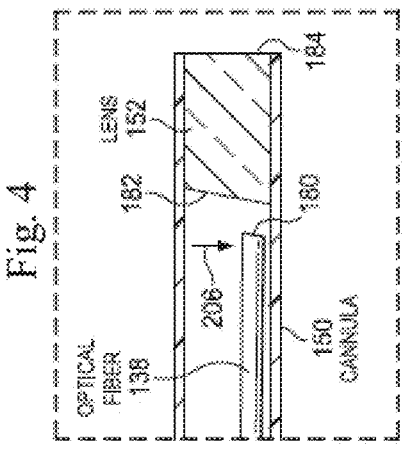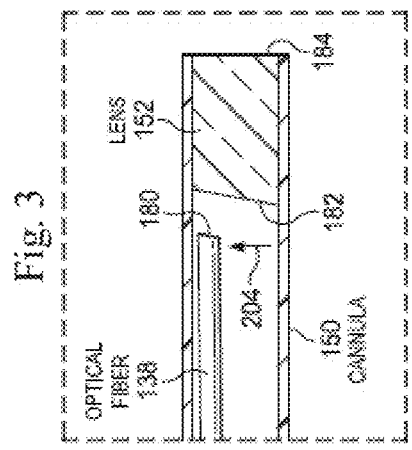

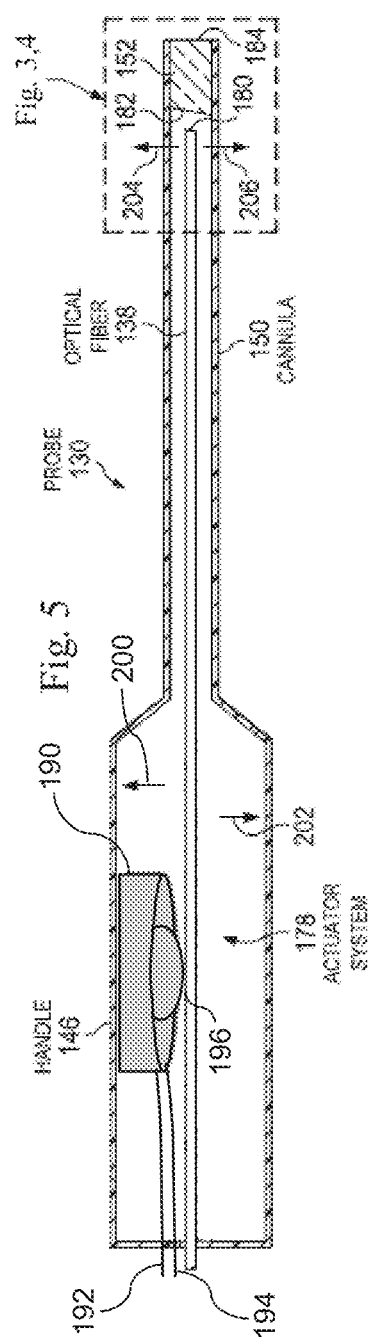

IMAGING PROBES AND ASSOCIATED DEVICES, SYSTEMS, AND METHODS UTILIZING SPEAKER ACTUATORS

TECHNICAL FIELD

Embodiments disclosed herein are related to devices, systems, and methods for scanning tissue with an optical coherence tomography (OCT) probe, and more particularly, to devices, systems, and methods that utilize an OCT probe having a displaceable fiber for ophthalmic imaging.

BACKGROUND

Optical Coherence Tomography (OCT) systems are used to capture and generate images of patient tissue layers. These systems often include OCT probes that can invasively penetrate tissue to obtain visualization of tissue within a patient. In ophthalmology, OCT probes are used to obtain detailed images of tissue about the eye or even forming a part of the eye, such as the retina.

In use, an optical light beam is directed through the probe at the tissue. A small portion of this light reflects from sub-surface features of the tissue and is collected through the same probe. Most of the light is not reflected but, rather, diffusely scatters at large angles. In conventional imaging, this diffusely scattered light contributes background noise that obscures an image. However, in OCT, a technique called interferometry records the optical path lengths of received photons, and provides data that rejects most of the photons that scatter multiple times before detection. This results in images that are clearer and that extend in the depth of the tissue.

The OCT probes often include a projecting cannula that can invasively penetrate patient tissue. The probe scans tissue by refracting the optical light beam through a lens disposed at an end of the cannula. A scan can include moving an optical fiber back and forth within the cannula to direct the light beam through the lens and at the tissue at different angles. The length and small diameter of the cannula make it difficult to move the fiber back and forth within the cannula. Further, the small amount of available space within the probe limits the types of actuators that can be utilized. Further still, the OCT probes and associated systems must be capable of being manufactured in a cost-effective manner, which includes the ability to make the probe as a disposable, one-time use device in some implementations.

SUMMARY

Embodiments disclosed herein are related to devices, systems, and methods that utilize a speaker to impart motion to an optical fiber positioned within an imaging probe.

Consistent with some embodiments, an ophthalmic imaging apparatus can be provided. The ophthalmic imaging apparatus can include an optical probe having a handle sized and shaped for handheld grasping by a user; and a cannula coupled to the handle, the cannula sized and shaped for insertion into an eye to be treated; an optical fiber positioned at least partially within the optical probe, the optical fiber configured to receive an imaging light from an imaging light source and guide the imaging light to an optical element positioned within the cannula of the optical probe; and an actuator system configured to impart motion to the optical fiber, the actuator system including a speaker positioned within the optical probe.

Consistent with some embodiments, an ophthalmic imaging system can be provided. The system can include an imaging light source configured to generate an imaging light; an optical guide in optical communication with the imaging light source, the optical guide configured to receive the generated imaging light from the imaging light source; and a probe in optical communication with the optical guide, the probe including a handle sized and shaped for handheld grasping by a user; and a cannula coupled to the handle, the cannula sized and shaped for insertion into an eye to be treated; an optical fiber positioned at least partially within the optical probe, the optical fiber configured to receive the imaging light from the optical guide and guide the imaging light to an optical element positioned within the cannula of the optical probe; and an actuator system configured to impart motion to the optical fiber, the actuator system including a speaker positioned within the optical probe.

Consistent with some embodiments, method of imaging an ophthalmic target with an imaging probe can be provided. The method can include guiding an imaging light to an optical fiber positioned within a cannula of the imaging probe with an optical guide; focusing the imaging light onto the ophthalmic target with an optical element positioned within the cannula of the imaging probe; and scanning the focused imaging light through a scanning pattern by moving a distal end of the optical fiber by actuating a speaker positioned within the imaging probe.

Additional aspects, features, and advantages of the present disclosure will become apparent from the following detailed description.

BRIEF DESCRIPTION OF THE DRAWINGS

FIG. 1 provides a diagrammatic schematic view of an eye under treatment and an OCT imaging system.

FIG. 2 provides a stylized illustration of a cross-sectional view of an imaging probe.

FIG. 3 provides a stylized illustration of a cross-sectional view of a distal portion of the imaging probe of FIG. 2 showing an optical fiber of the imaging probe in a first position.

FIG. 4 provides a stylized illustration of a cross-sectional view of the distal portion of the imaging probe of FIG. 2, similar to that of FIG. 3 but showing the optical fiber in a second position.

FIG. 5 provides a stylized illustration of a cross-sectional view of an imaging probe.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan tissue to obtain an OCT image. The probe can include a cannula configured to invasively penetrate patient tissue, such as the globe of an eye. The cannula can house a lens and an optical fiber. The fiber can direct light through the lens and capture reflected light that passes back through the lens. To obtain a scan of an area or a line of tissue, rather than merely a point, the fiber can be moved within the cannula relative to the lens to cause the light emerging from the lens to scan across the desired pattern. Because the cannula that penetrates the patient tissue can be desirably small in cross-section, moving the fiber within the cannula can be difficult. The small amount of available space within the probe can limit the types of actuators that can be utilized to impart movement to the fiber. In some instances it can be desirable to manufacture the probe, or at least a portion thereof, as a disposable component, which requires product designs having cost-effective manufacturing techniques.

Exemplary aspects described herein utilize a technique of moving all or some portion of the fiber within the probe using an actuator system positioned at least partially within the probe that overcomes one or more of the problems or limitations of previous approaches. The actuator system can include a speaker. The speaker can be positioned outside the cannula, such as in a handle of the probe, or inside the cannula. The distal end of the fiber can be moved by electrically activating the speaker. The fiber can be coupled to the speaker such that the movement of the speaker results in a corresponding movement of the distal end of the fiber. In some aspects, the actuator system can be configured to impart amplified motion to a distal section of the optical fiber. For example, the optical fiber can be positioned within the probe so that a distal end of the optical fiber extends past the speaker such that motion imparted to the distal section of the optical fiber is amplified relative to movement of a portion of the optical fiber proximate to and/or longitudinally coextensive with the speaker.

As a result, embodiments of the present disclosure (1) can be configured for use within the limited space available within an OCT probe, (2) can amplify the motion of the distal end of the fiber relative to the motion of the speaker, (3) can avoid the need for an actuator system that relies upon an interaction of mechanical components that can require very precise manufacturing tolerances, be difficult to assemble, and have a tendency to break at the sizes necessary for use in an OCT probe, (4) can impart repeatable motion to the optical fiber of the OCT probe suitable for optical scanning, and (5) can be manufactured in a cost-effective manner.

FIG. 1 provides a diagrammatic schematic view of an eye 100 under treatment and an OCT imaging system 120. The eye 100 can include sclera 102, a cornea 104, an anterior chamber 106, and a posterior chamber 108. A capsular bag 110 can be positioned in the posterior chamber 108. The eye 100 can include a retina 112. As discussed in greater detail below, the imaging system 120 can be configured to image portions of the eye 100, such as the retina 112. The imaging system 120 can include a light source 122, an optical coherence tomography (OCT) system 124, a controller 126, a user interface 128, and a probe 130. The light source 122 can be configured to provide imaging light that will be directed onto the target biological tissue by the probe 130. The light source 122 can be made up of super-luminescent diodes, ultra-short pulsed lasers, or supercontinuum lasers that provide relatively long wavelength light, such as between 700 nm and 1400 nm, between 700 nm and 900 nm, between 900 nm and 1200 nm, between 1000 nm and 1100 nm, between 1250 nm and 1450 nm, or between 1400 nm and 1600 nm. Imaging light reflected from the target biological tissue and captured by the probe 130 can be utilized to generate images of the target biological tissue.

The OCT system 124 can be configured to split the imaging light received from the light source 122 into the imaging beam that can be directed onto the target biological tissue by the probe 130 and a reference beam that can be directed onto a reference mirror. The OCT system 124 can be a spectral domain or a time domain system. The OCT system 124 can be further configured to receive the imaging light reflected from the target biological tissue and captured by the probe 130. The interference pattern between the reflected imaging light and the reference beam can be utilized to generate images of the target biological tissue. Accordingly, the OCT system 124 can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

The controller 126 can include a processor and memory, which may include one or more executable programs for controlling aspects of the light source 122, the user interface 128, and/or the probe 130, and for executing and performing functions and processes to carry out an OCT imaging procedure. For example, the controller 126 can be configured to control an actuation system of probe 130 configured to scan the imaging beam across the target biological tissue in some implementations.

One or more of the light source 122, the OCT system 124, the controller 126, and the user interface 128 can be implemented in separate housings communicatively coupled to one another or within a common console or housing. For example, in some implementations the light source 122, the OCT system 124, and the controller can be positioned within a console communicatively coupled to the user interface 128. The user interface 128 can be carried on or form part of the console. Further, the user interface 128, or at least part(s) thereof, can be separate from the console. The user interface 128 can include a display configured to present images to a user or a patient, and display tissue scanned by the probe 130 during an OCT imaging procedure. The user interface 128 can also include input devices or systems, including by way of non-limiting example, a keyboard, a mouse, a joystick, a touchscreen, dials, and buttons, among other input devices.

The probe 130 can be in optical communication with OCT system 124. In that regard, the probe 130 can be configured to present light from the light source 122 that passes through OCT system 124 onto the target biological tissue for the purpose of imaging the tissue. Further, the probe can be in electrical communication with the controller 126. In that regard, the controller 126 can control an actuation system of the probe 130 via electrical signals sent to the probe 130 in order to cause the actuation system to scan the imaging beam across the target biological tissue. A cable 132 can connect the probe 130 to the OCT system 124 and/or the controller 126. In that regard, cable 132 can include optical fiber(s), electrical conductor(s), insulator(s), shield(s), and/or other features configured to facilitate optical and/or electrical communication between the probe 130 and the OCT system 124 and/or the controller 126. Further, the cable 132 can include multiple, separate cables. For example, in some instances an optical cable connects the probe 130 to OCT system 124 and a separate electrical cable connects the probe 130 to controller 126.

The imaging system 120 can include a connector that is configured to facilitate removable coupling of the probe 130 and/or the cable 132 with the OCT system 124 and/or the controller 126. The connector is configured to facilitate mechanical, optical, and/or electrical coupling of the probe 130 and/or the cable 132 with the OCT system 124 and/or the controller 126. For example, an optical fiber 138 extending along the length of the probe 130 is optically coupled to the OCT system 124 via the coupling of the connector with the OCT system 124. The optical fiber 138 can be a single fiber or a fiber bundle. In some embodiments, the connector is configured to threadingly engage with the OCT system 124 and/or the controller 126. However, it is understood that any type of selective engagement feature(s) or connectors can be utilized, including without limitation press fit, luer lock, threads, and combinations thereof, among other connection types. In some aspects, connector is located proximate to the OCT system 124 and/or the controller 126. The selective engagement of the connector at the OCT system 124 and/or the controller 126 allows the entire probe 130 to be a disposable component configured for use in a single procedure.

The probe 130 can be sized and shaped to be handled by a surgeon and to protrude into a body of the patient. The probe 130 can include a proximal portion 142 and a distal portion 144. The proximal portion 142 can include a handle 146 sized and shaped for handheld grasping by a user. For example, the handle 146 can be sized and shaped for grasping by a single hand of the user. Further, the handle 146 can include a textured surface 148 (e.g., roughened, knurled, projections/recesses, tapers, other surface features, and/or combinations thereof) to enhance the user's grip on the handle 146. In use, the user can control the position of the distal portion 144 of the probe 130 by maneuvering the handle 146 such that the imaging light beam can be directed towards the target biological tissue.

The distal portion 144 of the probe 130 can be sized and shaped for insertion into the eye 100 to be treated. In the illustrated embodiment of FIG. 1, the distal portion 144 of the probe 130 includes a cannula 150. The cannula 150 can be sized and shaped for insertion through the sclera 102 of the eye 100 to facilitate imaging of the retina 112. The cannula 150 can be integrally formed with the handle 146. Alternatively, the cannula 150 and the handle 146 can be separate components fixedly secured to one another. An optical element 152, such as a lens, can be secured within the distal end of the cannula 150. The optical element 152 can be configured to focus the imaging light onto the target biological tissue, such as the retina 112. The optical element 152 can be, e.g., a gradient index (GRIN) lens, any other suitable lens, any suitable optical component(s), or a combination thereof. Depending upon the embodiment, the gradient index may be spherical, axial, or radial. The optical element 152 can also be a spherical lens. Other lens shapes may be used.

As will be discussed in greater detail below, the optical fiber 138 can be moved with respect to the optical element 152 by an actuator system disposed within the probe 130 to cause the imaging beam—as focused by the optical element 152—to scan across a portion of the target biological tissue. FIGS. 2 and 5 described below illustrate various embodiments of actuator systems in accordance with the present disclosure. In that regard, the actuator systems of the present disclosure can be positioned within the handle 146, within the cannula 150, and/or combinations thereof to move the optical fiber 138 across a desired scan pattern.

The distance of the focal point of the imaging beam from the distal end of the probe 130 can be determined by the optical element 152, a gap distance between the distal tip of the optical fiber 138 and a proximal face of the optical element 152, a numerical aperture of the optical fiber 138, and/or the wavelength of light of the imaging beam. For example, in some instances the focal power of the optical element 152 and/or the gap distance is selected to have a focus depth corresponding to likely distance of the distal end of the probe 130 from the target biological tissue during use. In some implementations of the probe 130 for retinal imaging, the focal point of the imaging beam can be between 1 mm and 20 mm, between 5 mm and 10 mm, between 7 mm and 8 mm, or approximately 7.5 mm beyond the distal end of the probe 130.

FIG. 2 provides a stylized illustration of a cross-sectional view of an embodiment of probe 130. As shown, the optical fiber 138 can extend along the length of the probe 130 through the handle 146 and the cannula 150. In the illustrated embodiment, an actuator system 178 can be positioned within the handle 146. The actuator system 178 can be configured to impart motion to the optical fiber 138 such that a distal end 180 of the optical fiber 138 moves with respect to the cannula 150 and the optical element 152 fixedly secured to the cannula. More specifically, the distal end 180 of the optical fiber 138 can be moved with respect to the optical element 152 to scan the imaging beam across a desired pattern with respect to the target biological tissue.

The optical element 152 can be configured to focus the imaging beam received from the optical fiber 138 onto the target biological tissue. In that regard, the optical element 152 can include a proximal face 182 and a distal face 184. The imaging beam can enter the optical element 152 through the proximal face 182 and leaves the optical element 152 through the distal face 184. As shown, the proximal face 182 of the optical element 152 can extend at an oblique angle with respect to the longitudinal axis of the cannula 150. By having the proximal face 182 oriented at an oblique angle, the amount of reflection resulting from the imaging beam entering the optical element 152 can be reduced. In other embodiments, the proximal face 182 extends perpendicular to the longitudinal axis of the cannula 150.

The distal end 180 the optical fiber 138 can be spaced from the proximal face 182 of the optical element 152. In that regard, the spacing between the distal end 180 of the optical fiber 138 and the proximal face 182 of the optical element 152 can be selected to achieve a desired optical performance (e.g., focal distance, focus size, etc.). The spacing between the distal end 180 of the optical fiber 138 and the proximal face 182 of the optical element 152 can also be selected to allow a desired range of motion of the optical fiber 138 within the cannula 150 without physically contacting the optical element 152. The optical element 152 can be mechanically coupled to the distal end 180 of the optical fiber 138 such that the optical element 152 moves with the distal end 180 of the optical fiber 138.

The actuator system 178 can be configured to impart motion to the optical fiber 138 such that the distal end 180 of the optical fiber 138 can be moved with respect to the optical element 152 to scan the imaging beam across a desired pattern with respect to the target biological tissue. The actuator system 178 can include a speaker 190 and electrical conductors 192, 194. The speaker 190 can be any suitable speaker type appropriately sized for positioning within an optical probe. In that regard, the speaker 190 may be configured to produce excitation or perturbation in the range between about 1 Hz and 100 Hz, between about 1 Hz and 50 Hz, between about 1 Hz and about 30 Hz, between about 5 Hz and 20 Hz, between about 10 Hz and 15 Hz, between about 1 Hz and 15 Hz, between about 100 Hz and 100 kHz, between about 2 kHz, and 20 kHz, etc., although other frequency ranges, both larger and smaller, are contemplated. The speaker 190 can include a diaphragm 196 that is displaced in response to the electrical signals received by the speaker from electrical conductors 192, 194. However, the diaphragm 196 of the speaker 190 may be actuated in a manner that does not impart the sound frequencies associated with normal operation of the speaker 190 in a typical audio setting. Rather, as discussed below, the speaker 190 may be actuated to displace the diaphragm 196 in a manner that imparts a desired motion profile to the optical fiber 138. In some embodiments, the speaker 190 can be positioned within the handle 146 and relative to the optical fiber 138 such that it is capable of producing sound frequencies associated with normal operation of the speaker 190. In some embodiments, the speaker 190 is positioned within the handle 146 and relative to the optical fiber 138 such that it is incapable of producing sound frequencies associated with normal operation of the speaker 190. For example, the optical fiber 138 can extend longitudinally through a recess in the speaker 190. While the speaker 190 cannot produce sound frequencies associated with a typical audio setting, the speaker 190 can produce excitation or perturbation to move the optical fiber 138 as described herein.

In some embodiments, all or some portion of the optical fiber 138 within the probe 190 (e.g., the distal end 180) moves, for example, between 10 μm and 500 μm, between 50 μm and 500 μm, between 100 gμm and 400 μm, or between 100 μm and 300 μm across the proximal face 182 of the optical element 152. The resulting optical scan is projected to the target biological tissue at a distance between, for example, 1 mm and 20 mm from the distal end of the cannula 150 (e.g., the focal point of the imaging beam, as described above). The linear extent of the imaging beam at the target biological tissue can be between 1 mm and 10 mm, between 1 mm and 8 mm, or between 1 mm and 5 mm. For example, there can be between approximately 50× and approximately 1000× multiplication of the distance the fiber moves across the proximal face 182 of the optical element 152 compared to the linear extent of the imaging beam at the target biological tissue.

The speaker 190 can be fixedly secured to a wall or other structure of handle 146, while the diaphragm 196 of the speaker 190 can be movable with respect to the handle 146. FIGS. 2 and 5 illustrate that the speaker 190 fixedly secured to a side wall of the handle 146 such that motion of the diaphragm 196 is perpendicular to the longitudinal axis of the optical fiber 138. In some embodiments, the speaker 190 is fixedly secured to the back wall of the handle 146 such that optical fiber 138 extends longitudinally through a recess in the speaker and/or the motion of the diaphragm 196 is parallel to the longitudinal axis of the optical fiber 138.

The actuator system 178 can be configured to cause the diaphragm 196 of the speaker 190 to move with respect to the handle 146 in response to selective, electric energization via conductors 192, 194. For example, by selectively applying a voltage to the speaker 190 via electrical conductors 192, 194 the resulting current causes the diaphragm 196 of the speaker 190 to be moved in either a first direction as indicated by arrow 200 or a second direction—opposite the first direction—as indicated by arrow 202. Accordingly, by controlling the magnitude and/or direction of the current passing through the speaker 190 via electrical conductors 192, 194, the magnitude and direction of the resulting movement of the diaphragm 196 of the speaker 190 can be controlled, which can be used to impart a desired motion profile to the distal end 180 of the optical fiber 138. The diaphragm 196 of the speaker 190 can configured to move in a direction perpendicular or parallel to a longitudinal axis of the optical fiber 138 between about 0.010 mm and about 1 mm, between about 0.010 mm and about 0.500 mm, between about 0.010 mm and about 0.200 mm, between about 0.010 mm and about 0.010 mm, etc., in response to activation of the speaker 190.

A proximal section of the optical fiber 138 can be coupled to the diaphragm 196 of the speaker 190 such that the optical fiber 138 moves with the diaphragm 196 of the speaker 190 in response to the application of an electric voltage to the speaker 190. A stiffening member 198 can be positioned adjacent to the optical fiber 138 and utilized to couple the optical fiber 138 to the diaphragm 196 of the speaker 190. The stiffening member can be secured to the optical fiber 138 using a suitable adhesive (e.g., glue, epoxy, etc.), mechanical connection, and/or combinations thereof. Similarly, the stiffening member can be secured to the diaphragm 196 of the speaker 190 using a suitable adhesive (e.g., glue, epoxy, etc.), mechanical connection, and/or combinations thereof. The stiffening member can also be secured to the handle 146, such as a proximal end of the handle 146, using a suitable adhesive (e.g., glue, epoxy, etc.), mechanical connection, and/or combinations thereof. The proximal section of the optical fiber 138 can also be secured to the handle 146, such as a proximal end of the handle 146, using a suitable adhesive (e.g., glue, epoxy, etc.), mechanical connection, and/or combinations thereof.

The stiffening member 198 can be formed of a material more rigid than the optical fiber 138. For example, the stiffening member can be formed of metal, hard plastic, ceramic, other suitable materials, and/or combinations thereof. The stiffening member can be a cylindrical tube positioned around a portion of the optical fiber 138. The stiffening member can also be a planar or arcuate plate structure extending around only a portion of the optical fiber 138. In that regard, the stiffening member can be configured to add rigidity to a portion of optical fiber 138 within an interior of the probe 130. The stiffening member can extend longitudinally along at least a portion of the optical fiber 138 such that the stiffening member extends entirely within the handle 146, extends entirely within the cannula 150, or partially extends in both the handle 146 and the cannula 150.

As shown, the optical fiber 138 can be fixedly coupled to the speaker 190 such that the distal end 180 of the optical fiber 138 extends distally beyond the diaphragm 196 of the speaker 190. In this manner, the distal end 180 of the optical fiber 138 can be cantilevered from the speaker 190. As a result, the motion profile of the distal end 180 of the optical fiber 138 can be amplified relative to the motion profile of the diaphragm 196 of the speaker 190. In other words, the movement of the distal end 180 of the optical fiber 138 can be greater than the corresponding movement of the diaphragm 196 of the speaker 190. For example, when the diaphragm 196 of the speaker 190 moves in the direction indicated by arrow 200, the distal end 180 of the optical fiber will move as indicated by arrow 204 a greater distance in the same direction. Similarly, when the diaphragm 196 of the speaker 190 moves in the direction indicated by arrow 202, the distal end 180 of the optical fiber will move as indicated by arrow 206 a greater distance in the same direction. The ratio of the movement of the distal end 180 of the optical fiber 138 to the movement of the diaphragm 196 of the speaker 190 can be between 1.01:1.0 and 10.0:1.0, between 1.1:1.0 and 5.0:1.0, or between 1.5:1.0 and 2.0:1.0. Accordingly, the resultant movement of the distal end 180 of the optical fiber 138 can be more than 1%, 10%, 20%, 50%, 100%, 500%, or 1000% greater than the movement of the diaphragm 196 of the speaker 190.

In some instances, the motion profile of the distal end 180 of the optical fiber can simulate a lever arm action with a pivot point within the handle 146 of the probe 130. For example, the pivot point can be defined by the connection of the proximal section of the optical fiber 138 and/or the stiffening member 198 to the handle 146. As another example, the pivot point can be defined by the connection of the optical fiber 138 and/or the stiffening member 198 to the diaphragm 196 of the speaker 190.

Generally, the actuator system 178 can be configured to move the speaker 190 from a neutral position to one or more activated positions. As a result, the actuator system 178 can be likewise configured to move the distal end 180 of the optical fiber 138 from a neutral position to one or more activated positions. In a neutral position, the optical fiber 138 can be positioned at any location within the lumen of the cannula 140. For example, all or some portion of the optical fiber 138 within the probe 190 can be coaxial with the longitudinal axis of the cannula 150 (as shown in, e.g., FIG. 2), proximate to and/or in contact with one wall of the cannula 150 (as shown in, e.g., FIGS. 3 and 4), etc. Similarly, in one or more activated positions, the optical fiber 138 can be coaxial with the longitudinal axis of the cannula 150 (as shown in, e.g., FIG. 2), proximate to and/or in contact with one wall of the cannula 150 (as shown in, e.g., FIGS. 3 and 4), etc.

For example, FIG. 2 illustrates an embodiment where the neutral position of the optical fiber 138 can be coaxial with the longitudinal axis of the cannula 150. The actuator system 178 can be configured to move the diaphragm 196 of the speaker 190 and, thereby, the distal end 180 of the optical fiber 138 from the position coaxial with the longitudinal axis to a first activated (as depicted in FIG. 3) and a second activated position (as depicted in FIG. 4). Current can flow through the electrical conductors 192, 194 and the speaker 190 in a first direction to urge the diaphragm 196 in direction 200 and, thereby, the distal end 180 of the optical fiber 138 in direction 204 towards the first activated position of FIG. 3. Current can flow through the electrical conductors 192, 194 and the speaker 190 in the opposing direction to urge the diaphragm 196 in direction 202 and, thereby, the distal end 180 of the optical fiber 138 in direction 206 towards the second activated position of FIG. 4.

By oscillating the optical fiber between the first and second activated positions illustrated in FIGS. 3 and 4, the imaging beam can be scanned across the target biological tissue, such as the retina. In some implementations, the actuator system 178 is configured to oscillate the distal end 180 of the optical fiber 138 within a frequency range between about 1 Hz and 100 Hz, between about 1 Hz and 50 Hz, between about 1 Hz and about 30 Hz, between about 5 Hz and 20 Hz, between about 10 Hz and 15 Hz, between about 1 Hz and 15 Hz, etc., although other frequency ranges, both larger and smaller, are contemplated.

The positions of the distal end 180 of the optical fiber 138 depicted in FIGS. 3 and 4 can also be the neutral position for the actuator system 178. In that regard, the distal end 180 of the optical fiber 138 can begin in the position of FIG. 3 or FIG. 4 and then move to the position of FIG. 4 or FIG. 3, respectively, upon energization of the speaker 190. In such implementations, current can flow through the electrical conductors 192, 194 and the speaker 190 in a manner to urge the diaphragm 196 and, thereby, the distal end 180 of the optical fiber 138 towards the opposite position. By stopping the current and/or reversing the current, the diaphragm 196 and the distal end 180 of the optical fiber 138 can be urged back towards the starting position. In that regard, the elastic force of the diaphragm 196 of the speaker 190, the optical fiber 138, and/or the stiffening member 198 can cause them to return to the original starting position.

FIG. 5 provides a stylized illustration of a cross-sectional view of the imaging probe 130 in accordance with another aspect of the present disclosure. The probe 130 of FIG. 5 includes many features similar to those discussed above that will not be repeated here for sake of brevity. The actuator system 178 of the probe 130 of FIG. 5 can include the speaker 190 with the diaphragm 196 coupled directly to the optical fiber 138. Accordingly, the imaging probe 130 of FIG. 5 does not include the stiffening member 198. A proximal section of the optical fiber can be secured to the diaphragm 196 of the speaker 190 using a suitable adhesive (e.g., glue, epoxy, etc.), mechanical connection, and/or combinations thereof.

The motion profiles discussed in the context of the actuator systems above focused on linear displacement of the optical fiber 138 within cannula, which can be utilized to produce a corresponding linear scan of the imaging beam across the target biological tissue. In other embodiments, the actuator system includes speakers oriented perpendicular to one another that can be selectively energized to scan the optical fiber 138 and the imaging beam across a two-dimensional scanning pattern. One of the two speakers can be configured to impart motion to the optical fiber 138 along a first axis and the other of the two speakers can be configured to impart motion to the optical fiber 138 along a second axis perpendicular to the first axis. The two-dimensional scanning pattern can include a spiral, a raster, a constant-radius asterisk, a multiple-radius asterisk, a multiply folded path, other two-dimensional scan patterns, other patterns, and/or combinations thereof.

Embodiments as described herein may provide an imaging probe having an actuator that utilizes a speaker to impart motion to an optical fiber positioned within the imaging probe. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic imaging apparatus, comprising:
    an optical probe having
        a handle sized and shaped for handheld grasping by a user; and
        a cannula coupled to the handle, the cannula sized and shaped for insertion into an eye to be treated;
    an optical fiber positioned at least partially within the optical probe, the optical fiber configured to receive an imaging light from an imaging light source and guide the imaging light to an optical element positioned within the cannula of the optical probe; and
    an actuator system configured to impart motion to the optical fiber, the actuator system including a speaker positioned within the optical probe.

2. The apparatus of claim 1, wherein:
    the actuator system is configured to impart amplified motion to a distal section of the optical fiber.

3. The apparatus of claim 2, wherein:
    the optical fiber is coupled to a diaphragm of the speaker so that a distal end of the optical fiber extends past a distal end of the speaker such that motion imparted to the distal end of the optical fiber is amplified relative to the movement of the diaphragm of the speaker.

4. The apparatus of claim 1, wherein:
a proximal section of the optical fiber is fixedly secured to a diaphragm of the speaker.

5. The apparatus of claim 1, further comprising:
a stiffening member positioned within the optical probe, the stiffening member positioned between the speaker and the optical fiber.

6. The apparatus of claim 1, wherein:
a proximal section of the optical fiber is affixed to the handle.

7. The apparatus of claim 1, wherein:
a diaphragm of the speaker is configured to move relative to the handle in response to activation of the speaker.

8. The apparatus of claim 7, wherein:
the speaker is configured to produce excitation in a frequency range between about 1 Hz and about 100 Hz.

9. The apparatus of claim 7, wherein:
the diaphragm of the speaker is configured to move in a direction perpendicular to a longitudinal axis of the optical fiber between about 0.010 mm and about 0.500 mm in response to activation of the speaker.

10. The apparatus of claim 1, wherein:
the optical probe is disposable.

11. The apparatus of claim 1, wherein:
the optical element comprises a gradient index (GRIN) lens.

12. The apparatus of claim 1, wherein:
the optical element is mechanically coupled to a distal end of the optical fiber so that the optical element moves with the distal end of the optical fiber.

13. The apparatus of claim 1, wherein:
the optical element is fixedly secured to the distal portion of the cannula.

14. The apparatus of claim 1, wherein:
the actuation system is configured to impart motion to the optical fiber to scan the imaging light along a scanning pattern with a linear extent at a target biological tissue between 1 mm and 5 mm at a distance between 5 mm and 10 mm from a distal end of the cannula.

15. The apparatus of claim 1, wherein:
the actuator system is configured to impart motion to the optical fiber to scan the imaging light over a two-dimensional scanning pattern.

16. The apparatus of claim 15, wherein:
the two dimensional scanning pattern comprises at least one of a spiral, a raster, a constant-radius asterisk pattern, a multiple-radius asterisk pattern, and a multiply folded path.

17. The apparatus of claim 15, wherein:
the actuator system comprises a second speaker, wherein second speaker is configured to impart motion to the optical fiber along a first axis and the other speaker is configured to impart motion to the optical fiber along a second axis perpendicular to the first axis.

18. An ophthalmic imaging system, comprising:
an imaging light source configured to generate an imaging light;
an optical guide in optical communication with the imaging light source, the optical guide configured to receive the generated imaging light from the imaging light source; and
a probe in optical communication with the optical guide, the probe including
a handle sized and shaped for handheld grasping by a user; and
a cannula coupled to the handle, the cannula sized and shaped for insertion into an eye to be treated;
an optical fiber positioned within the probe, the optical fiber configured to receive the imaging light from the optical guide and guide the imaging light to an optical element positioned within the cannula; and
an actuator system including a speaker configured to impart motion to the optical fiber.

19. The ophthalmic imaging system of claim 18, further comprising:
a controller in communication with the light source, the controller configured to control actuation of the imaging light source for an optical coherence tomography (OCT) imaging procedure.

20. The ophthalmic imaging system of claim 19, wherein:
the controller is further configured to process data obtained by the probe and output imaging data to a display in communication with the controller.

21. A method of imaging an ophthalmic target with an imaging probe, comprising:
guiding an imaging light to an optical fiber positioned within a cannula of the imaging probe with an optical guide;
focusing the imaging light onto the ophthalmic target with an optical element positioned within the cannula of the imaging probe; and
scanning the focused imaging light through a scanning pattern by moving a distal end of the optical fiber by actuating a speaker positioned within the imaging probe.

* * * * *